United States Patent [19]

Okamoto et al.

[11] 4,073,892

[45] * Feb. 14, 1978

[54] N²-ALKOXYNAPHTHYLSULFONYL-L-ARGININAMIDES AND THE PHARMACEUTICALLY ACCEPTABLE SALTS THEREOF

[75] Inventors: Shosuke Okamoto, 15-1i, Asahigaoka 3-chome, Tarumi, Kobe, Hyogo, Japan; Akiko Hijikata, Kobe, Japan; Ryoji Kikumoto, Machida, Japan; Yoshikuno Tamao, Yokohama, Japan; Kazuo Ohkubo, Machida, Japan; Tohru Tezuka, Yokohama, Japan; Shinji Tonomura, Tokyo, Japan

[73] Assignees: Mitsubishi Chemical Industries Limited, Tokyo; Shosuke Okamoto, both of Japan

[ * ] Notice: The portion of the term of this patent subsequent to Oct. 25, 1994, has been disclaimed.

[21] Appl. No.: 760,738

[22] Filed: Jan. 19, 1977

Related U.S. Application Data

[63] Continuation-in-part of Ser. No. 638,985, Dec. 9, 1975, which is a continuation-in-part of Ser. No. 671,436, March 29, 1976, which is a continuation-in-part of Ser. No. 622,390, Oct. 14, 1975, abandoned.

[30] Foreign Application Priority Data

| Nov. 8, 1974 | Japan | 49-128774 |
| Nov. 8, 1974 | Japan | 49-128775 |
| Nov. 29, 1974 | Japan | 49-136695 |
| Nov. 29, 1974 | Japan | 49-136697 |
| Feb. 25, 1975 | Japan | 50-023268 |
| Feb. 26, 1975 | Japan | 50-023635 |

[51] Int. Cl.² .................... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS

| 3,131,174 | 4/1964 | Schwyer | 260/112.5 R |
| 4,018,913 | 4/1977 | Okamoto et al. | 260/112.5 R |
| 4,018,915 | 4/1977 | Okamoto et al. | 260/112.5 R |

*Primary Examiner*--Delbert R. Phillips
*Attorney, Agent, or Firm*—Oblon, Fisher, Spivak, McClelland & Maier

[57] ABSTRACT

N²-alkoxynaphthylsulfonyl-L-argininamides and the pharmaceutically acceptable salts thereof have been found to be effective as pharmaceutical agents for the inhibition and suppression of thrombosis in mammals, and are prepared by reacting an N²-alkoxynaphthylsulfonyl-L-arginyl halide with an N-substituted amino acid or an ester thereof.

10 Claims, No Drawings

ID# $N^2$-ALKOXYNAPHTHYLSULFONYL-L-ARGININAMIDES AND THE PHARMACEUTICALLY ACCEPTABLE SALTS THEREOF

CROSS REFERENCE TO RELATED APPLICATIONS

This application is a continuation-in-part of U.S. application Ser. No. 638,985 filed Dec. 9, 1975, which, in turn is a continuation-in-part of U.S. application Ser. No. 671,436, filed on Mar. 29, 1976, which, in turn, is a continuation-in-part of U.S. application Ser. No. 622,390, filed on Oct. 14, 1975, now abandoned.

BACKGROUND OF THE INVENTION

1. Field of the Invention

This invention relates to the discovery of certain new and useful $N^2$-alkoxynaphthylsulfonyl-L-argininamides and the pharmaceutically acceptable salts thereof, which are of special value in view of their outstanding antithrombotic properties and low toxicities.

2. Description of the Prior Art

In the past, there have been many attempts to obtain new and improved agents for the treatment of thrombosis. The $N^2$-(p-tolylsulfonyl)-L-arginine esters have been found to be one type of agent which can be used and these have been found to be effective in dissolving blood clots. (U.S. Pat. No. 3,622,615, issued Nov. 23, 1971).

One family of compounds which have been found to be particularly useful as highly specific inhibitors of thrombin for the control of thrombosis is the $N^2$-dansyl-L-arginine ester or amide. (Our pending U.S. application Ser. No. 496,939, filed Aug. 13, 1974 now U.S. Pat. No. 3,978,045).

However, there is a continuing need for a highly specific inhibitor on thrombin for the control of thrombosis, which exhibits lower toxicity.

SUMMARY OF THE INVENTION

It has now been discovered that $N^2$-alkoxynaphthylsulfonyl-L-argininamides exhibit antithrombotic activity and even lower toxicity levels at the same relative potencies, as compared with the $N^2$-dansyl-L-arginine ester or amide.

The compounds of this invention can be represented by the formula (I):

$$\begin{array}{c} HN \\ \diagdown \\ \phantom{HN}C-N-CH_2CH_2CH_2CHCON \\ \diagup \phantom{C-}| \phantom{-CH_2CH_2CH_2CH}| \phantom{CON} \diagdown \\ H_2N \phantom{C-N-}H \phantom{CH_2CH_2CH_2CH}HNSO_2 \phantom{N}(CH_2)_n-COOR_3 \\ \phantom{H_2N \phantom{C-N-}H \phantom{CH_2CH_2CH_2CH}}| \\ \phantom{H_2N \phantom{C-N-}H \phantom{CH_2CH_2CH_2CH}}R_1 \end{array} \quad (I)$$

wherein $R_1$ is naphthyl substituted with at least one $C_1$–$C_5$ alkoxy; $R_2$ is selected from the group consisting of $C_2$–$C_{10}$ alkyl, $C_3$–$C_{10}$ alkenyl, $C_3$–$C_{10}$ alkynyl, $C_2$–$C_{10}$ alkoxyalkyl, $C_8$–$C_{15}$ alpha-carboxyaralkyl, $C_2$–$C_{10}$ alkylsulfinylalkyl, $C_1$–$C_{10}$ hydroxyalkyl, $C_2$–$C_{10}$ carboxyalkyl, $C_3$–$C_{10}$ alkoxycarbonylalkyl and $C_1$–$C_{10}$ haloalkyl; $R_3$ is selected from the group consisting of hydrogen, $C_1$–$C_{10}$ alkyl, $C_6$–$C_{10}$ aryl, $C_7$–$C_{12}$ aralkyl and 5-indanyl; and $n$ is an integer of 1, 2 or 3.

Also encompassed within this invention are pharmaceutically acceptable salts thereof.

This invention also relates to a method for inhibiting activity and suppressing activation of thrombin in vivo in mammals, which comprises administering to a mammal, a pharmaceutically (antithrombatically) effective amount of an $N^2$-alkoxynaphthyl-sulfonyl-L-argininamide or the pharmaceutically acceptable salts thereof.

Another aspect of this invention relates to a process for producing $N^2$-alkoxynaphthylsulfonyl-L-argininamides, which comprises reacting an $N^2$-alkoxynaphthylsulfonyl-L-arginyl halide with a corresponding N-substituted amino acid or an ester thereof.

DETAILED DESCRIPTION OF THE PREFERRED EMBODIMENTS

This invention relates to a group of $N^2$-alkoxynaphthylsulfonyl-L-argininamides of the formula (I):

$$\begin{array}{c} HN \\ \diagdown \\ \phantom{HN}C-N-CH_2CH_2CH_2CHCON \\ \diagup \phantom{C-}| \phantom{-CH_2CH_2CH_2CH}| \phantom{CON} \diagdown \\ H_2N \phantom{C-N-}H \phantom{CH_2CH_2CH_2CH}HNSO_2 \phantom{N}(CH_2)_n-COOR_3 \\ \phantom{H_2N \phantom{C-N-}H \phantom{CH_2CH_2CH_2CH}}| \\ \phantom{H_2N \phantom{C-N-}H \phantom{CH_2CH_2CH_2CH}}R_1 \end{array}$$

wherein $R_1$ is an alkoxynaphthyl wherein the alkoxy groups have 1–5 (preferably 1–3) carbon atoms, such as methoxy, ethoxy, propoxy, isopropoxy, butoxy, sec-butoxy, tert-butoxy, pentyloxy or the like. Preferred are those naphthyl groups having one or two alkoxy substituents, when two or more alkoxy groups are present, each may be the same or different; $R_2$ is selected from the group consisting of $C_2$–$C_{10}$ alkyl, such as ethyl, propyl, butyl, isobutyl, pentyl, hexyl, octyl, decyl or the like, alkenyl of 3–10 (preferably 3–6) carbon atoms, such as allyl, 2-butenyl, 3-butenyl, 2-pentenyl or the like, alkynyl of 3–10 (preferably 3–6) carbon atoms, such as 2-propynyl, 2-butynyl, 3-butynyl or the like, alkoxyalkyl of 2–10 (preferably 2–6) carbon atoms, such as methoxymethyl, ethoxymethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, α-carboxyaralkyl of 8–15 (preferably 8–12) carbon atoms, such as α-carboxybenzyl, α-carboxyphenethyl or the like; alkylsulfinylalkyl of 2–10 (preferably 2–6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1–10 (preferably 1–6) carbon atoms, such as hydroxymethyl, 2-hydroxyethyl, 3-hydroxypropyl, 2hydroxypropyl, 4-hydroxybutyl, 3-hydroxybutyl, 5-hydroxypentyl or the like, carboxyalkyl of 2–10 (preferably 2–7) carbon atoms, such as carboxymethyl, 2-carboxyethyl, 2-carboxypropyl, 3-carboxypropyl, 1-carboxybutyl, 2-carboxybutyl, 4-carboxybutyl or the like, alkoxycarbonylalkyl of 3–10 (preferably 3–8) carbon atoms, such as methoxycarbonylmethyl, 2-ethoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, and haloalkyl of 1–10 (preferably 1–5) carbon atoms such as chloromethyl, 2-chloroethyl, 2-bromoethyl, 2-chloropropyl, 3-chloropropyl, 2-chlorobutyl, 4-chlorobutyl or the like; $R_3$ is selected from the group consisting of hydrogen, $C_1$–$C_{10}$ alkyl, such as methyl, ethyl, propyl, butyl, tert-butyl, hexyl, octyl, decyl or the like, $C_6$–$C_{10}$ aryl, such as phenyl, m-tolyl, naphthyl, p-tolyl, ethylphenyl, butyl-phenyl or the like, aralkyl of 7-12 (preferably 7-10) carbon atoms, such as benzyl, phenethyl or the like, and 5-indanyl; and $n$ is an integer of 1, 2 or 3.

Suitable illustrations of $R_1$ in the above formula (I) are 5-methoxy-1-naphthyl, 6-methoxy-2-naphthyl, 7-methoxy-2-naphthyl, 4,6-dimethoxy-2-naphthyl, 7-methoxy-2-naphthyl, 4,6-dimethoxy-2-naphthyl, 6,7-dimethoxy-2-naphthyl and 6,7-diethoxy-2-naphthyl.

Suitable illustrations of $R_2$ in the above formula (I) are $C_2$-$C_{10}$ alkyl, such as propyl, butyl, isobutyl, pentyl, hexyl and octyl, $C_3$-$C_6$ alkenyl such as allyl, $C_3$-$C_6$ alkynyl, such as 2-propynyl, $C_2$-$C_6$ alkoxyalkyl, such as 2-methoxyethyl, 2-methoxypropyl, 2-ethoxyethyl and 3-methoxypropyl, $C_8$-$C_{12}$ α-carboxyalkyl, such as α-carboxyphenethyl, $C_2$-$C_6$ alkylsulfinylalkyl, such as 2-methylsulfinylethyl, $C_1$-$C_6$ hydroxyalkyl, such as 2-hydroxyethyl and 3-hydroxybutyl, $C_2$-$C_7$ carboxyalkyl, such as 1-carboxybutyl, $C_3$-$C_8$ alkoxycarbonylalkyl, such as 2-ethoxycarbonylethyl. Suitable examples of $R_3$ in the above formula (I) are hydrogen, $C_1$-$C_{10}$ alkyl, such as methyl, ethyl, tert-butyl and octyl, $C_6$-$C_{10}$ aryl, such as phenyl and m-tolyl, $C_7$-$C_{10}$ aralkyl, such as benzyl and 5-indanyl.

Illustrative of suitable $N^2$-alkoxynaphthylsulfonyl-L-argininamides of sufficient activity of this invention are the following:

$N^2$-(6, 7-dimethoxy-2-naphthylsulfonyl)-L-arginyl-N-propylglycine
$N^2$-(6, 7-dimethoxy-2-naphthylsulfonyl)-L-arginyl-N-propyl-glycine tert-butyl ester
$N^2$-(6, 7-dimethoxy-2-naphthylsulfonyl)-L-arginyl-N-butylglycine
$N^2$(6, 7-dimethoxy-2-npahthylsulfonyl)-L-arginyl-N-butylglycine tert-butyl ester
$N^2$-(6, 7-dimethoxy-2-naphthylsulfonyl)-L-arginyl-N-isobutylglycine
$N^2$-(6, 7-dimethoxy-2-naphthylsulfonyl)-L-arginyl-N-isobutylglycine tert-butyl ester
$N^2$-(6, 7-dimethoxy-2-naphthylsulfonyl)-L-arginyl-N-pentylglycine
$N^2$-(6, 7-dimethoxy-2-naphthylsulfonyl)-L-arginyl-N-pentylglycine tert-butyl ester
$N^2$-(6, 7-dimethoxy-2-naphthylsulfonyl)-L-arginyl-N-hexylglycine
$N^2$-(6, 7-dimethoxy-2-naphthylsulfonyl)-L-arginyl-N-hexylglycine tert-butyl ester
$N^2$-(6, 7-dimethoxy-2-naphthylsulfonyl)-L-arginyl-N-octylglycine
$N^2$-(6, 7-dimethoxy-2-naphthylsulfonyl)-L-arginyl-N-octylglycine tert-butyl ester
$N^2$-(6, 7-dimethoxy-2-naphthylsulfonyl)-L-arginyl-N-(2-methoxyehtyl) glycine
$N^2$-(6, 7-dimethoxy-2-naphthylsulfonyl)-L-arginyl-N-(2-methoxyethyl) glycine ethyl ester
$N^2$-(6, 7-dimethoxy-2-naphthylsulfonyl)-L-arginyl-N-(2-methoxyehtyl)-β-alanine
$N^2$-(6, 7-dimethoxy-2-naphthylsulfonyl)-L-arginyl-N-(2-methoxyethyl)-β-alanine ethyl ester
$N^2$-(6, 7-dimethoxy-2-naphthylsulfonyl)-N-(2-methoxyethyl)-N-(3-carboxypropyl)-L-argininamide
$N^2$-(6, 7-dimethoxy-2-naphthylsulfonyl)-N-(2-methoxyethyl)-N-(3-tert-butoxycarbonylpropyl)-L-argininamide
$N^2$-(6, 7-dimethoxy-2-naphthylsulfonyl)-N-(3-methoxypropyl)glycine
$N^2$-(6, 7-dimethoxy-2-naphthylsulfonyl)-N-(3-methoxypropyl)glycine tert-butyl ester
$N^2$-(6, 7-dimethoxy-2-naphthylsulfonyl)-L-arginyl-N-(2-ethoxyethyl)-β-alanine
$N^2$-(6, 7-dimethoxy-2-naphthylsulfonyl)-L-arginyl-N-(2-ethoxyethyl)-β-alanine tert-butyl ester
$N^2$-(4, 6-dimethoxy-2-naphthylsulfonyl)-L-arginyl-N-(2-methoxyethyl) glycine
$N^2$-(4, 6-dimethoxy-2-naphthylsulfonyl)-L-arginyl-N-(2-methoxyethyl) glycine ethyl ester
$N^2$-(4, 6-dimethoxy-2-naphthylsulfonyl)-L-arginyl-N-butylglycine
$N^2$-(4, 6-dimethoxy-2-naphthylsulfonyl)-L-arginyl-N-butylglycine tert butyl ester
$N^2$-(6, 7-diethoxy-2-naphthylsulfonyl)-L-arginyl-N-(2-methoxyethyl) glycine
$N^2$-(6, 7-diethoxy-2-naphthylsulfonyl)-L-arginyl-N-(2-methoxyethyl) glycine tert-butyl ester
$N^2$-(6, 7-diethoxy-2-naphthylsulfonyl)-L-arginyl-N-butylglycine
$N^2$-(6, 7-diethoxy-2-naphthylsulfonyl)-L-arginyl-N-butylglycine tert-butyl ester
$N^2$-(6-methoxy-2-naphthylsulfonyl)-L-arginyl-N-butylglycine
$N^2$-(6-methoxy-2-naphthylsulfonyl)-L-arginyl-N-butylglycine tert-butyl ester
$N^2$-(6-methoxy-2-naphthylsulfonyl)-L-arginyl-N-(2-methoxyethyl) glycine
$N^2$-(6-methoxy-2-naphthylsulfonyl)-L-arginyl-N-(2-methoxyethyl) glycine tert-butyl ester
$N^2$-(7-methoxy-2-naphthylsulfonyl)-L-arginyl-N-(2-methoxyethyl) glycine
$N^2$-(7-methoxy-2-naphthylsulfonyl)-L-arginyl-N-(2-methoxyethyl) glycine ethyl ester
$N^2$-(7-methoxy-2-naphthylsulfonyl)-L-arginyl-N-propylglycine
$N^2$-(7-methoxy-2-naphthylsulfonyl)-L-arginyl-N-propylglycine tert-butyl ester
$N^2$-(7-methoxy-2-naphthylsulfonyl)-L-arginyl-N-butylglycine
$N^2$-(7-methoxy-2-naphthylsulfonyl)-L-arginyl-N-butylglycine tert-butyl ester
$N^2$-(7-methoxy-2-naphthylsulfonyl)-L-arginyl-N-pentylglycine
$N^2$-(7-methoxy-2-naphthylsulfonyl)-L-arginyl-N-pentylglycine tert-butyl ester
$N^2$-(5-methoxy-1-naphthylsulfonyl)-L-arginyl-N-(2-methoxyethyl) glycine
$N^2$-(5-methoxy-1-naphthylsulfonyl)-L-arginyl-N-(2-methoxyethyl) glycine tert-butyl ester
$N^2$-(5-methoxy-1-naphthylsulfonyl)-L-arginyl-B-butylglycine
$N^2$-(5-methoxy-1-naphthylsulfonyl)-L-arginyl-N-butylglycine tert-butyl ester
$N^2$-(5-methoxy-1-naphthylsulfonyl)-L-arginyl-N-(2-methoxyethyl)-β-alanine
$N^2$-(5-methoxy-1-naphthylsulfonyl)-L-arginyl-N-(2-methoxyethyl)β-alanine tert-butyl ester
$N^2$-(6, 7-dimethoxy-2-naphthylsulfonyl)-L-arginyl-N-(2-ethoxycarbonylethyl)glycine
$N^2$-(6, 7-dimethoxy-2-naphthylsulfonyl)-L-arginyl-N-(2-methoxyethyl)glycine octyl ester
$N^2$-(6, 7-dimethoxy-2-naphthylsulfonyl)-L-arginyl-N-(2-methoxyethyl)glycine benzyl ester
$N^2$-(6, 7-dimethoxy-2-naphthylsulfonyl)-L-arginyl-N-(2-methoxyethyl) glycine m-tolyl ester
$N^2$-(6, 7-dimethoxy-2-naphthylsulfonyl)-L-arginyl-N-(2-methoxyethyl) glycine 5-indanyl ester
$N^2$-(6, 7-dimethoxy-2-naphthylsulfonyl)-L-arginyl-N-(2-methoxypropyl)glycine N²-(7-methoxy-2-naphthylsulfonyl)-L-arginyl-N-(2-methylsulfinylethyl)glycine
N²-(6, 7-dimethoxy-2-naphthylsulfonyl)-L-arginyl-N-(2-hydroxyethyl)glycine
N²-(6, 7-dimethoxy-2-naphthylsulfonyl)-L-arginyl-N-allylglycine
N²-(6, 7-dimethoxy-2-naphthylsulfonyl)-L-arginyl-N-(2-propynyl)glycine
N²-(6, 7-dimethoxy-2-naphthylsulfonyl)-L-arginyl-N-(1-carboxybutyl)glycine
N²-(6, 7-dimethoxy-2-naphthylsulfonyl)-L-arginyl-N-(3-hydroxybutyl)glycine
N²-(6, 7-dimethoxy-2-naphthylsulfonyl)-L-arginyl-N-(α-carboxyphenethyl)glycine Of the compounds of this invention, it will be understood that the following compounds are most preferred due to their high level of antithrombotic activity and low level of toxicity.
N²-(6, 7-dimethoxy-2-naphthylsulfonyl)-L-arginyl-N-butylglycine
N²-(7-methoxy-2-naphthylsulfonyl)-L-arginyl-N-butylglycine
N²-(6, 7-dimethoxy-2-naphthylsulfonyl)-L-arginyl-N-(2-methoxyethyl)glycine
N²-(6, 7-dimethoxy-2-naphthysulfonyl)-L-arginyl-N-(2-methoxyethyl)glycine ethyl ester
N²-(4, 6-dimethoxy-2-naphthylsulfonyl)-L-arginyl-N-(2-methoxyethyl)glycine
N²-(7-methoxy-2-naphthylsulfonyl)-L-arginyl-N-(2-methoxyethyl)glycine The pharmaceutically acceptable salts of the above compounds are of course also included within the scope of this invention.

The above compounds are intended only to illustrate the variety of structures which can be used in the process of this invention, and the above listing is not to be construed as limiting the scope of the invention.

These typical compounds are highly potent in their antithrombotic activity.

For the preparation of the compounds of this invention, various methods can be employed depending upon the particular starting materials and/or intermediates involved. Successful preparation of these compounds is possible by way of several synthetic routes which are outlined below.

(a) Condensation of an L-argininamide with an alkoxy-naphthalenesulfonyl halide
This process may be illustrated as follows:

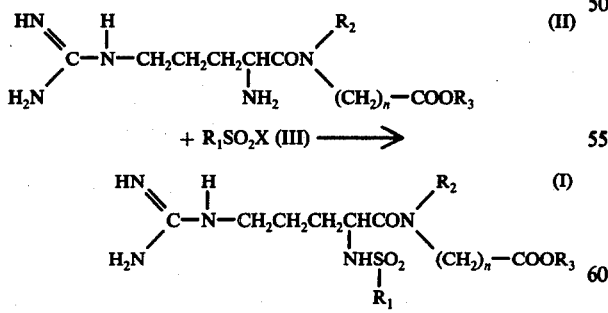

In the above formulas, $R_1$, $R_2$, $R_3$ and $n$ are as defined hereinabove, and X is halogen.

The N²-alkoxynaphthylsulfonyl-L-argininamide (I) is prepared by the condensation of an L-argininamide (II) with a substantially equimolar amount of an alkoxynaphthalenesulfonyl halide (III), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include benzene-diethyl ether, diethyl ether-water and dioxane-water.

After the reaction is complete, the formed salt is extracted with water, and the solvent is removed by such standard means as evaporation under reduced pressure to give the N²-alkoxynaphthylsulfonyl-L-argininamide (I), which can be purified by trituration or recrystallization from a suitable solvent, such as diethyl ether-tetrahydrofuran, diethyl ether-methanol and water-methanol, or may be chromatographed on silica gel.

The L-argininamides (II) starting materials required for the condensation reaction can be prepared by protecting the guanidino and α-amino groups of the L-arginine via nitration, acetylation, formylation, phthaloylation, trifluoroacetylation, p-methoxy-benzyloxycarbonylation, benzoylation, benzyloxycarbonylation, tert-butoxycarbonylation or tritylation and then condensing the formed N^G-substituted-N²-substituted-L-arginine with a corresponding N-substituted amino acid or an ester thereof by such a conventional process as the acid chloride method, azide method, mixed anhydride method activated ester method or carbodimide method, and thereafter selectively removing the protective groups.

(b) Removal of the N^G-substituent from an N^G-substituted-N²-alkoxynaphthylsulfonyl-L-argininamide.
This process may be illustrated as follows:

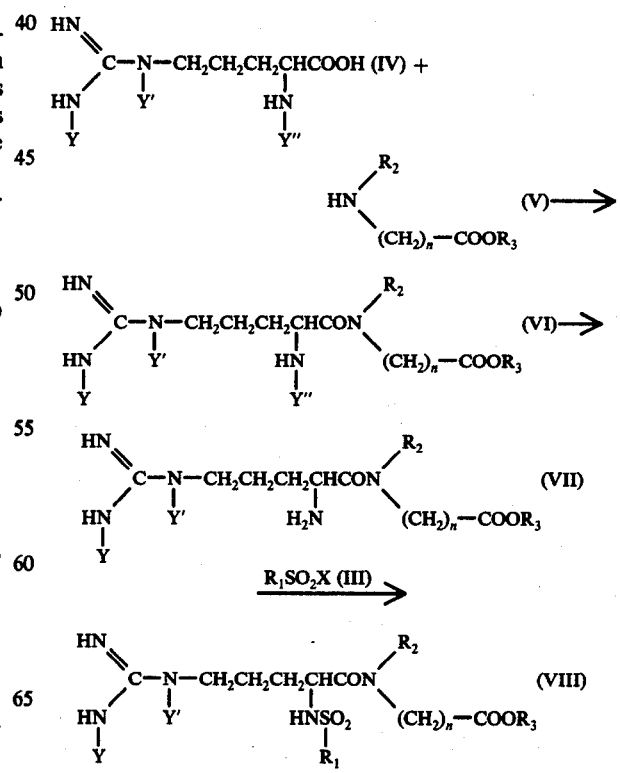

-continued

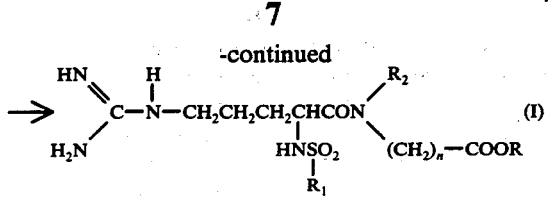

In the above formulas, $R_1$, $R_2$, $R_3$, X and n are as defined hereinabove; Y'' is a protective group for the amino group, such as benzyloxycarbonyl or tert-butoxycarbonyl; and Y and Y' are hydrogen and protective groups for the guanidino group, such as nitro, tosyl, trityl, oxycarbonyl or the like. At least one of the Y and Y' is a protective group for the guanidino group.

The $N^2$-alkoxynaphthylsulfonyl-L-argininamide (I) is prepared by removing the $N^G$-substituent from an $N^G$-substituted-$N^2$-alkoxynaphthylsulfonyl-L-argininamide (VII) by means of acidolysis or hydrogenolysis.

The acidolysis is generally effected by contacting the $N^G$-substituted-$N^2$-alkoxynaphthylsulfonyl-L-argininamide (VIII) and an excess of an acid such as hydrogen fluoride, hydrogen chloride, hydrogen bromide or trifluoroacetic acid, without a solvent or in a solvent, such as in ether (tetrahydrofuran, dioxane), an alcohol (methanol, ethanol) or acetic acid at a temperature of $-10°$ C to $100°$ C, and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-alkoxynaphthylsulfonyl-L-argininamides (I), which can be easly converted to a free amide by neutralization.

The removal of the nitro group and the oxycarbonyl group, e.g., benzyloxycarbonyl, p-nitrobenzyloxy-carbonyl, is readily accomplished by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of $0°$ C to the boiling temperature of the solvent for a period of 2 hours to 120 hours.

The hydrogen pressure is not critical, and atmospheric pressure is sufficient.

The $N^2$-alkoxynaphthylsulfonyl-L-argininamides (I) are isolated by filtration of the catalyst followed by evaporation of the solvent.

The $N^2$-alkoxynaphthylsulfonyl-L-argininamides can be purified in the same manner as described above.

The $N^G$-substituted-$N^2$-alkoxynaphthylsulfonyl-L-argininamides (VIII) starting materials can be prepared by condensing an $N^G$-substituted-$N^2$-substituted L-arginine (IV) (generally the $N^2$-substituent is a protective group for the amino group, such as benzyloxycarbonyl, tert-butoxycarbonyl or the like) and a corresponding N-substituted amino acid or an ester thereof (V) via the azide method, mixed anhydride method, activated ester method, carbodiimido method or the like, selectively removing only the $N^2$-substituent of an $N^G$-substituted-$N^2$-substituted L-argininamide (VI) by means of catalytic hydrogenolysis or acidolysis, and then condensing the thus obtained $N^G$-substituted-L-argininamide (VII) with an alkoxynaphthalenesulfonyl halide (III), preferably a chloride in the presence of a base in a solvent. These reaction conditions are as described above in the condensation of an L-arginininamide with an alkoxynaphthalenesulfonyl halide, and the removal of the $N^G$-substituent from an $N^G$-substituted-$N^2$-alkoxynaphthylsulfonyl-L-argininamide.

(c) Condensation of an $N^2$-alkoxynaphthylsulfonyl-L-arginyl halide with an N-substituted amino acid or an ester thereof.

This process may be illustrated as follows:

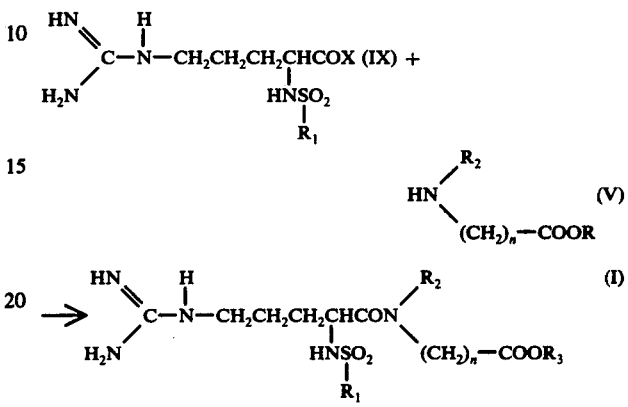

In the above formulas, $R_1$, $R_2$, $R_3$, X and n are as defined hereinabove.

The $N^2$-alkoxynaphthylsulfonyl-L-arginamide (I) is prepared by the condensation of an $N^2$-alkoxynaphthylsulfonyl-L-arginyl halide (IX), preferably a chloride with at least an equimolar amount of an N-substituted amino acid or an ester thereof (V).

The condensation reaction can be carried out without an added solvent. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the $N^2$-alkoxynaphthylsulfonyl-L-arginyl halide (IX).

Preferred condensation reaction temperatures are in the range of from $-10°$ C to room temperature. The reaction time is not critical, but varies with the N-substituted amino acid or the ester thereof (V) employed. In general, a period of from 5 minutes to 10 hours is operable.

The obtained $N^2$-alkoxynaphthylsulfonyl-L-argininamide can be isolated and purified in the same manner as described above.

The $N^2$-alkoxynaphthylsulfonyl-L-arginyl halides (IX) starting materials required for the condensation reaction can be prepared by reacting an $N^2$-alkoxynaphthylsulfonyl-L-arginine with at least an equimolar amount of halogenating agent such as thionyl chloride, phoshporous oxychloride, phosphorus trichloride, phosphorous pentachloride or phosphorus tribromide. The halogenation can be carried out with or without an added solvent.

The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-alkoxynaphthylsulfonyl-L-arginine. Preferred reaction temperatures are in the range of $-10°$ C to room temperature. The reaction time is not critical, but varies with the halogenating agent and reaction temperature. In general, a period of 15 minutes to 5 hours is operable.

The $N^2$-alkoxynaphthylsufonly-L-arginine compounds which are the starting material for the preparation of the $N^2$-alkoxynaphthylsulfonyl-L-arginyl halides (IX) can be prepared by the condensation of L-arginine with a substantially equimolar amount of the alkoxynaphthalenesulfonyl halide (III) by a method similar to that described in the condensation of an L-argininamide with a naphthalenesulfonyl halide.

(d) Guanidylation of an $N^2$-alkoxynaphthylsulfonyl-L-ornithinamide or an acid addition salt thereof This process may be illustrated as follows:

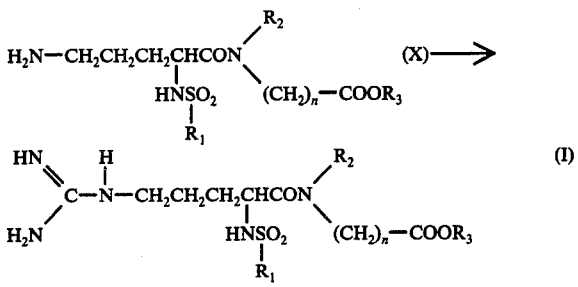

In the above formulas, $R_1$, $R_2$, $R_3$ and $n$ are as defined hereinabove.

The $N^2$-alkoxynaphthylsulfonyl-L-argininamide (I) is prepared by guanidylating an $N^2$-alkoxynaphthylsulfonyl-L-ornithinamide (X) with an ordinary guanidylating agents such as an O-alkylisourea, S-alkylisothiourea, 1-guanyl-3, 5-dimethylpyrazole or carbodiimide. The preferred guanidylating agents are the O-alkylisourea and the S-alkylisothiaourea.

The guanidylation of the $N^2$-alkoxynaphthylsulfonyl-L-ornithinamide (X) with the O-alkylisourea or S-alkylisothiourea is generally effected in a solvent in the presence of a base at a temperature of from 0° to the boiling temperature of the solvent for a period of from 30 minutes to 50 hours.

Examples of the preferred bases are triethylamine, pyridine, sodium, hydroxide and sodium methoxide.

The base is used in an amount of 0.01 to 0.1 equivalent to the $N^2$-alkoxynaphthylsulfonyl-L-ornithinamide.

Examples of the preferred solvent are water, water-ethanol and water-dioxane.

After the reaction is complete, the $N^2$-alkoxynaphthylsulfonyl-L-argininamide (I) is isolated by evaporation of the solvent followed by removal of the excess base and the formed salt by a water wash.

It is well recognized in the art that an ester derivative of the $N^2$-alkoxynaphthylsulfonyl-L-argininamide (I) wherein $R_3$ is alkyl, aryl, aralkyl or 5-indanyl, can be prepared from a carboxylic acid derivative of the $N^2$-alkoxynaphthylsulfonyl-L-argininamide wherein $R_3$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-alkoxynaphthylsulfonyl-L-argininamide (I) of this invention forms acid addition salts with any of a variety of inorganic and organic acids. Some of the $N^2$-alkoxynaphthylsulfonyl-L-argininamide containing a free carboxyl group, wherein $R_3$ is hydrogen, forms salts any of a variety of inorganic and organic bases. The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-alkoxynaphthylsulfonyl-L-argininamides, and the salts thereof of this invention are characterized by highly specific inhibitory activity in mammals against thrombin as well as by their substantial lack of toxicity, and therefore these compounds are useful in the determination of thrombin in blood as diagnostic reagents, and/or for the medical control of prevention of thrombosis.

The antithrombotic activities of the $N^2$-alkoxynaphthylsulfonyl-L-argininamide of this invention were compared with that of a known antithrombotic agent, $N^2$-(p-tolysulfonyl)-L-arginine methyl ester, by determining the fibrinogen coagulation time. The measurement of the fibrinogen coagulation time was conducted as follows: An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50–55 seconds.

The experimental results are summarized in Table 1. The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolylsulfonyl)-L-arginine methyl ester, was 1,100 um.

The inhibitors are shown in Table 1 by indicating $R_1$, $R_2$, $R_3$ and $n$ in the formula (I) and the addition moiety.

When a solution containing an $N^2$-alkoxynaphthylsulfonyl-L-argininamide of this invention was administered intravenously into animal bodies, the high antithrombotic activity in the circulating blood was maintained for from one to three hours. The halflife for decay of the antithrombotic compounds of this invention in circulating blood was shown to be approximately 60 minutes; the physiological conditions of the host animals (mammals such as rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight. Representative $LD_{50}$ values, for example, for $N^2$-(6, 7-dimethoxy-2-naphthylsulfonyl)-L-arginyl-N-(2-methoxyethyl)glycine, $N^2$-(6, 7-dimethoxy-2-naphthylsulfonyl)-L-arginyl-N-(2-ethoxyethyl)-$\beta$-alanine, $N^2$-(4, 6-dimethoxy-2-naphthylsulfonyl)-L-arginyl-N-(2-methoxyethyl)glycine, $N^2$-(7-methoxy-2-naphthylsulfonyl)-L-arginyl-N-(2-methoxyethyl)glycine are 1,900–2,400, 660–1,000, 660–1,000, 2,000 milligrams per kilogram, respectively.

On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents of this invention may be administered to mammals, including humans, alone or in combination with pharmaceutically acceptable carriers, the proportion of which is determined by the solubility and chemical nature of the compound, chosen route of administration and standard pharmaceutical practice, For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable for humans, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

$N^2$-(4, 6-dimethoxy-2-naphthylsulfonyl)-L-arginyl-N-arginyl-N-(2-methoxyethyl)glycine (A) L-arginyl-N-(2-methoxyethyl)glycine ethyl ester hydrochloride:

To a solution of 4.0 g of $N^G$-nitro-L-arginyl-N-(2-methoxyethyl) glycine ethyl ester hydrochloride in 50 ml of ethanol was added 0.5 g of palladium-black and then the mixture was shaken in a hydrogen atmosphere for 150 hours at room temperature. At the end of this period, the ethanol solution was filtered to remove the catalyst and evaporated to give an oily product. Reprecipitation with ethanol-ethyl ether gave 3.0 g (81%) of L-arginyl-N-(2-methoxyethyl)glycine ethyl ester hydrochloride in the form of a powder.

(B) $N^2$-(4, 6-dimethoxy-2-naphthylsulfonyl)-L-arginyl-N-(2-methoxyethyl)glycine ethyl ester:

To a well stirred solution of 2.00 g of L-arginyl-N-(2-methoxyethyl) glycine ethyl ester hydrochloride and 1.95 g of $K_2CO_3$ in 20 ml of water and 10 ml of dioxane was added dropwise a solution of 2.17 g of 4, 6-dimethoxy-2-naphthalenesulfonyl chloride in 30 ml of dioxane over a period of 30 minutes while maintaining the temperature at 0° C. The reaction mixture was stirred for an additional 5 hours at room temperature. At the end of this period, the solvent was evaporated and the residue taken up in 50 ml of chloroform. The chloroform solution was filtered to remove the insoluble material and dried over anhydrous sodium sulfate. Addition of 150 ml of diethyl ether to the chloroform solution resulted in a precipitate which was separated by decantation and purified by reprecipitation with ethanol-diethyl ether to give 2.31 g (72 percent) of $N^2$-(4, 6-dimethoxy-2-naphthylsulfonyl)-L-arginyl-N-(2-methoxyethyl)glycine ethyl ester.

For analysis of the product, a portion of the product was converted to the flavianate; M.P. 225° – 227° C, I.R. (KBr): 3,375, 3,200, 1,742 $cm^{-1}$. Analysis Calcd. for $C_{25}H_{37}N_5O_8S \cdot C_{10}H_6N_2O_8S$ (percent): C, 47.67; H, 4.92; N, 11.12 Found (percent): c, 47.62; H, 4.84; N, 11.18.

(C) $N^2$-(4, 6-dimethoxy-2-naphthylsulfonyl)-L-arginyl-N-(2-methoxyethyl) glycine:

A solution of 2.5 g of $N^2$-(4, 6-dimethoxy-2-naphthylsulfonyl)-L-arginyl-N-(2-methoxyethyl)glycine ethyl ester in 5 ml of ethanol and 7 ml of 1N NaOH solution was stirred for 30 hours at room temperature. At the end of this period, the solution was concentrated to 5 ml, chromatographed on 80 ml of Daiaion ® SK 102 ion exchange resin (200–300 mesh, H+ form, manufactured by Mitsubishi Chemical Industries Limited) packed in water, washed with water, and eluted with 3% ammonium hydroxide solution. The fraction eluted from 3% ammonium hydroxide solution was evaporated to dryness, and the residue was purified by reprecipitation with ethanol-diethyl ether to give 1.32 g (72 percent) of $N^2$-(4, 6-dimethoxy-2-naphthylsulfonyl)-L-arginyl-N-(2-methoxyethyl)glycine as an amorphous solid, I.R. (KBr): 3,360, 3,180, 1,610 $cm^{-1}$. Analysis Calcd. for $C_{23}H_{33}N_5O_8S$ (percent): C, 51.20; H, 6.17; N, 12.98 Found (percent): C, 51.31; H, 6.01; N, 12.67.

EXAMPLE 2

$N^2$-(6, 7-dimethoxy-2-naphthylsulfonyl)-L-arginyl-N-(2-methoxyethyl)glycine (A) $N^G$-nitro-$N^2$-(tert-butoxycarbonyl)-L-arginyl-N-(2-methoxyethyl)glycine ethyl ester:

To a stirred solution of 28.3 g of $N^G$-nitro-$N^2$-(tert-butoxycarbonyl)-L-arginine in 450 ml of dry tetrahydrofuran were added in turn 12.4 ml of triethylamine and 12.4 ml of isobutyl chloroformate while keeping the temperature at −5° C. After 15 minutes, to this was added 14.2 g of N-(2-methoxyethyl)glycine ethyl ester, and the mixture was stirred for 15 minutes at −5° C. At the end of this period, the reaction mixture was warmed to room temperature. The solvent was evaporated and the residue taken up in 400 ml of ethyl acetate, and washed successively with 200 ml of water, 100 ml of 5% sodium bicarbonate solution, 100 ml of 10% citric acid solution and 200 ml of water. The ethyl acetate solution was dried over anhydrous sodium sulfate. Upon evaporation of the solvent, the residue was dissolved in 20 ml of chloroform, and the solution was applied to a column (80 cm × 6 cm) of 500 g of silica gel packed in chloroform. The product was eluted first with chloroform, and then 3% methanolchloroform. The fraction eluted from 3% methanol-chloroform was evaporated to dryness to give 25.8 g (63 percent) of $N^G$-nitro-$N^2$-(tert-butoxycarbonyl)-L-arginyl-N-(2-methoxyethyl)glycine ethyl ester in the form of a syrup. I.R. (KBr): 3,300, 1,740 1,690 cm$^{+1}$.

(B) $N^G$-nitro-L-arginyl-N-(2-methoxyethyl)glycine ethyl ester hydrochloride:

To a stirred solution of 29.8 g of $N^G$-nitro-$N^2$-(tert-butoxycarbonyl)-L-arginyl-N-(2-methoxyethyl)glycine ethyl ester in 50 ml of ethyl acetate was added 80 ml of 10% dry CHl-ethyl acetate at 0° C. After 3 hours, to this solution was added 200 ml of dry ethyl ether to precipitate a viscous oily product.

This was filtered and washed with dry ethyl ether to give 24.1 g of $N^G$-nitro-L-arginyl-N-(2-methoxyethyl)glycine ethyl ester hydrochloride as an amorphous solid.

(C) $N^G$-nitro-$N^2$-(6, 7-dimethoxy-2-naphthylsulfonyl)-L-arginyl-N-(2-methoxyethyl)glycine ethyl ester:

To a stirred solution of 4.0 g of $N^G$-nitro-L-arginyl-N-(2-methoxyethyl)glycine ethyl ester hydrochloride in 20 ml of water and 20 ml of dioxane were added in turn 2.5 g of sodium bicarbonate, and 3.5 g of 6, 7-dimethoxy-2-naphthalenesulfonyl chloride in 30 ml of dioxane at 5° C, and stirring was continued for 3 hours at room temperature. At the end of this period, the solvent was evaporated and the residue dissolved in 40 ml of chloroform, and washed with 10 ml of 1N hydrochloric acid solution and 20 ml of water.

The chloroform solution was dried over anhydrous sodium sulfate. Upon evaporation of the solvent, the residue was chromatographed on 50 g of silica gel packed in chloroform, washed with chloroform and eluted with 3% methanol-chloroform. The fraction eluted from 3% methanol-chloroform was evaporated to give 5.3 g (87 percent) of $N^G$-nitro-$N^2$-(6, 7-dimethoxy-2-naphthylsulfonyl)-L-arginyl-N-(2-methoxyethyl)glycine ethyl ester in the form of an amorphous solid. I.R. (KBr): 3,240, 1,740, 1,630 cm$^{-1}$.

(d) $N^2$-(6, 7-dimethoxy-2-naphthylsulfonyl)-L-arginyl-N-(2-methoxyethyl)glycine ethyl ester:

To a solution of 3.00 g of $N^G$-nitro-$N^2$-(6, 7-dimethoxy-2-naphthylsulfonyl)-L-arginyl-N-(2-methoxyethyl)glycine ethyl ester in 50 ml of ethanol and 0.5 ml of acetic acid was added 0.5 g of palladium-black and then the mixture was shaken in a hydrogen atmosphere for 100 hours at room temperature. At the end of this period, the ethanol solution was filtered to remove the catalyst and evaporated to give an oily product. Reprecipitation with ethanol-diethyl ether gave 2.53 g (91%) of $N^2$-(6, 7-dimethoxy-2-naphthylsulfonyl)-L-arginyl-N-(2-methoxyethyl)glycine ethyl ester.

For analysis of the product, a portion of the product was converted to the flavianate; M.P. 185° C, I.R. (KBr): 3,375, 3,200, 1,740 cm$^{-1}$.

Analysis Calcd. for $C_{25}H_{37}N_5O_8S \cdot C_{10}H_6N_2O_8S$ (percent): C, 47.67; H, 4.92; N, 11.12 Found (percent): C, 47.64; H, 4.81; N, 11.12.

$N^2$-(6, 7-dimethoxy-2-naphthylsulfonyl)-L-arginyl-N-(2-methoxyethyl)glycine was prepared by hydrolysis of its ethyl ester in a manner analogous to Example 1.

I.R. (KBr): 3,380, 3,180, 1,630 cm$^{-1}$.

Analysis Calcd. for $C_{23}H_{33}N_5O_8S$ (percent): C, 51.20; H, 6.17; N, 12.98 Found (percent): C, 50.93; H, 6.02; N, 12.63.

EXAMPLE 3

$N^2$-(6, 7-dimethoxy-2-naphthylsulfonyl)-L-arginyl-N-butylglycine (A) $N^2$-(6, 7-dimethoxy-2-naphthylsulfonyl)-L-arginine:

To a well stirred solution of 83.6 g of L-arginine in 800 ml of 10% potassium carbonate solution was added 114.7 g of 6, 7-dimethoxynaphthalenesulfonyl chloride in 800 ml of benzene. The reaction mixture was stirred at 60° C for 5 hours, during which time the product precipitated. After one hour at room temperature, the precipitate was filtered and washed successively with benzene and water to give 129 g (76 percent) of $N^2$-(6, 7-dimethoxy-2-naphthylsulfonyl)-L-arginine, M.P. 252–5° C.

(B) $N^2$-(6, 7-dimethoxy-2-naphthylsulfonyl)-L-arginyl chloride

A suspension of 2.00 g of $N^2$-(6, 7-dimethoxy-2-naphthylsulfonyl)-L-arginine in 20 ml of thionyl chloride was stirred for 2 hours at room temperature. Addition of cold dry diethyl ether resulted in a precipirate which was collected by filtration and washed several times with dry diethyl ether to give $N^2$-(6, 7-dimethoxy-2-naphthylsulfonyl)-L-arginyl chloride.

(C) $N^2$-(6, 7-dimethoxy-2-naphthylsulfonyl)-L-arginyl-N-butylglycine tert-butyl ester To a stirred solution of 2.64 g of N-butylglycine tert-butyl ester in 20 ml of chloroform was carefully added $N^2$-(6, 7-dimethoxy-2-naphthylsulfonyl)-L-arginyl chloride obtained above. The reaction mixture was allowed to stand at room temperature for one hour. At the end of this period, the reaction mixture was washed twice with 20 ml of saturated sodium chloride solution and evaporated to dryness.

The residue was triturated with a small amount of water to give a crystalline material. This was collected by filtration and recrystallized from ethanol-diethyl ether to give 2.28 g (82 percent) of $N^2$-(6, 7-dimethoxy-2-naphthylsulfonyl)-L-arginyl-N-butylglycine tert-butyl ester, M.P. 164°–166° C, I.R. (KBr): 3,390, 3,165, 1,735, 1,370 cm$^{-1}$.

Analysis Calcd. For $C_{28}H_{43}O_7N_5S \cdot \frac{1}{2}H_2SO_3$ (percent): C, 52.98; H, 7.00; N, 11.04 Found (percent): C, 52.69; H, 6.98; N, 10.86.

(D) $N^2$-(6, 7-dimethoxy-2-naphthylsulfonyl)-L-arginyl-N-butylglycine

To a solution of 2.00 g of $N^2$-(6, 7-dimethoxy-2-naphthylsulfonyl)-L-arginyl-N-butylglycine tert-butyl ester in 20 ml of chloroform was added 50 ml of 15% HCl-ethyl acetate. The reaction mixture was stirred for 5 hours at room temperature. At the end of this period, the reaction mixture was evaporated to dryness. The residue was washed several times with dry diethyl ether and chromatographed on 80 ml of Daiaion ® SK 102 ion exchange resin (200–300 mesh, H+ form, manufactured by Mitsubishi Chemical Industries Limited) packed in water, washed with water and eluted with 3% ammonium hydroxide solution.

The fraction eluted from 3% ammonium hydroxide solution was evaporated to dryness to give 1.43 g (79 percent) of $N^2$-(6, 7-dimethoxy-2-naphthylsulfonyl)-L-arginyl-N-butyglycine as an amorphous solid. I.R. (KBr): 3,360, 3,140, 1,622 cm$^{-1}$.

Analysis Calcd. for $C_{24}H_{35}N_5O_7S$ (percent): C, 53.62; H, 6.56; N, 13.03 Found (percent): C, 53.48, H, 6.43; N, 12.98.

EXAMPLE 4

(A) $N^2$-(6, 7-dimethoxy-2-naphthylsulfonyl)-L-arginyl-N-(2-methoxypropyl)glycine ethyl ester To a stirred solution of 1.3 g of N-(2-methoxypropyl)glycine ethyl ester and 1.7 ml of triethylamine in 50 ml of chloroform, which was cooled in an ice-salt bath, was added in portions $N^2$-(6, 7-dimethoxy-2-naphthylsulfonyl)-L-arginyl chloride which was obtained in Example 3. The reaction mixture was stirred overnight at room temperature. At the end of this period, 50 ml of chloroform was added and the chloroform solution was washed twice with 50 ml of saturated sodium chloride solution, dried over anhydrous sodium sulfate and evaporated in vacuo. The oily residue was washed with ether to give 2.4 g of powdery $N^2$-(6, 7-dimethoxy-2-naphthylsulfonyl)-L-arginyl-N-(2-methoxypropyl)glycine ethyl ester.

(B) $N^2$-(6, 7-diemthoxy-2-naphthylsulfonyl)-L-arginyl-N-(2-methoxypropyl)glycine ethyl ester.

(B) $N^2$-(6, 7-dimethoxy-2-naphthylsulfonyl)-L-arginyl-N-(2-methoxy-propyl)glycine A solution of 2.3 g of $N^2$-(6, 7-dimethoxy-2-naphthylsulfonyl)-L-arginyl-N-(2-methoxypropyl)glycine ethyl ester in 15 ml of methanol and 5 ml of 2N sodium hydroxide solution was warmed at 40° C and held at that temperature for 10 hours. At the end of this period, the reaction mixture was concentrated and chromatographed on 200 ml of Daiaion ® SK 102 ion exchange resin (200–300 mesh, H+ form, manufactured by Mitsubishi Chemical Industries Limited) packed in water, washed with ethanol-water (1:4) and eluted with ethanol-water-NH$_4$OH (10:9:1). The main fraction was evaporated to dryness and washed with ether to give 1.8 g of $N^2$-(6, 7-dimethoxy-2-naphthylsulfonyl)L-arginyl-N-(2-methoxypropyl)glycine as an amorphous solid.

I.R. (KBr): 3,350 (broad), 1,620 cm$^{-1}$.

Analysis Calcd. for $C_{24}H_{35}N_5O_8S$ (percent): C, 52.06; H, 6.38; N, 12.65 Found (percent): C, 52.40; H, 6.37; N, 12.73.

EXAMPLE 5

(A) $N^2$-(6, 7-dimethoxy-2-naphthylsulfonyl)-L-arginyl-N-(2-methoxyethyl)glycine chloride hydrochloride:

A suspension of 2.00 g of $N^2$-(6, 7-dimethoxy-2-naphthylsulfonyl)-L-arginyl-N-(2-methoxyethyl)glycine in 20 ml of thionyl chloride was stirred for 2 hours at room temperature. Addition of cold dry ethyl ether resulted in a precipitate which was collected by filtration and washed several times with dry ethyl ether to give $N^2$-(6, 7-dimethoxy-2-naphthylsulfonyl)-L-arginyl-N-(2-methoxyethyl)glycyl chloride hydrochloride.

(B) $N^2$-(6, 7-dimethoxy-2-naphthylsulfonyl)-L-arginyl-N-(2-methoxyethyl)glycine m-tolyl ester hydrochloride:

A mixture of 2.00 g of m-cresol and $N^2$-(6, 7-dimethoxy-2-naphthylsulfonyl)-L-arginyl-N-(2-methoxyethyl)glycyl chloride hydrochloride obtained above was heated at 90° C for 50 minutes. At the end of this period, the reaction mixture was cooled, washed several times with dry ethyl ether, and then dissolved in 10 ml of dry ethyl alcohol. Addition of cold dry ethyl ether resulted in a precipitate which was washed several times with dry ethyl ether to give 2.12 g (86 percent) of $N^2$-(6, 7-dimethoxy-2-naphthylsulfonyl)-L-arginyl-N-(2-methoxyethyl)glycine m-tolyl ester hydrochloride in the form of a powder.

I.R. (KBr): 3,250, 3,100, 1,740, 1,640 cm$^{-1}$.

Various other $N^2$-alkoxynaphthylsulfonyl-L-argininamides or acid addition salts thereof were synthesized in accordance with the procedure of the above examples, and the test results are summarized in Table 1.

-continued

| | COMPOUND $HN\underset{H_2N}{\overset{}{\diagup}}C-N-CH_2CH_2CH_2CHCON\underset{R_1}{\overset{R_2}{\diagdown}}$ $H-N-SO_2\underset{R_1}{\overset{(CH_2)_n-COOR_3}{\diagup}}$ (I) | | | | | | Concentration Required to Prolong The Coagulation Time By A Factor of Two (μM) | Preparation Process (Ex. No.) | m.p. (°C) | Elemental Analysis Upper: Calculated Lower: Found | | | I.R. (KBr) (cm$^{-1}$) |
|---|---|---|---|---|---|---|---|---|---|---|---|---|---|
| Sample No. | $R_1$ | $R_2$ | $R_3$ | n | Addition moeity | | | | | C | H | N | |
| 14 | " | —CH$_2$CH$_2$OCH$_3$ | —C$_2$H$_5$ | 1 | 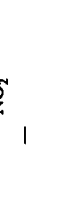 | | 1.5 | 2 | 185 | 47.67<br>47.64 | 4.92<br>4.81 | 11.12<br>11.12 | 3,375<br>3,200<br>1,740 |
| 15 | " | —CH$_2$CH$_2$OCH$_3$ | H | 2 | — | | 2.5 | 2 | powder | 52.07<br>52.21 | 6.37<br>6.04 | 12.67<br>12.51 | 3,380<br>3,200<br>1,620 |
| 16 | " | —CH$_2$CH$_2$OCH$_3$ | —C$_2$H$_5$ | 2 | — | | | 2 | powder | 53.69<br>53.53 | 6.76<br>6.69 | 12.04<br>12.38 | 3,380<br>3,200<br>1,740 |
| 17 | " | —CH$_2$CH$_2$OCH$_3$ | H | 3 | — | | 2.5 | 3 | powder | 52.90<br>52.71 | 6.57<br>6.43 | 12.34<br>12.46 | 3,350<br>3,160<br>1,640 |
| 18 | " | —CH$_2$CH$_2$OCH$_3$ | —C(CH$_3$)$_3$ | 3 | ½H$_2$SO$_3$ | | | 3 | powder | 52.40<br>52.16 | 6.96<br>7.13 | 10.54<br>10.28 | 3,340<br>3,160<br>1,736<br>1,380 |
| 19 | " | —CH$_2$CH$_2$—OCH$_3$ | H | 1 | — | | 5 | 3 | powder | 52.07<br>51.91 | 6.37<br>6.19 | 12.65<br>12.38 | 3,360<br>3,160<br>1,620 |
| 20 | " | —CH$_2$CH$_2$—OCH$_3$ | —C(CH$_3$)$_3$ | 1 | ½H$_2$SO$_3$ | | | 3 | powder | 51.68<br>51.43 | 6.82<br>6.66 | 10.76<br>10.58 | 3,380<br>3,160<br>1,740<br>1,370 |
| 21 | " | —CH$_2$CH$_2$OC$_2$H$_5$ | H | 2 | — | | 4 | 3 | powder | 52.90<br>52.59 | 6.57<br>6.41 | 12.34<br>12.16 | 3,360<br>3,160<br>1,640 |
| 22 | " | —CH$_2$CH$_2$OC$_2$H$_5$ | —C(CH$_3$)$_3$ | 2 | ½H$_2$SO$_3$ | | | 3 | powder | 52.98<br>52.73 | 7.00<br>7.00 | 11.04<br>10.82 | 3,377<br>3,160<br>1,740<br>1,368 |
| 23 |  | —CH$_2$CH$_2$OCH$_3$ | H | 1 | — | | 4 | 1 | powder | 51.20<br>51.31 | 6.17<br>6.01 | 12.98<br>12.67 | 3,360<br>3,180<br>1,610 |
| 24 |  | —CH$_2$CH$_2$OCH$_3$ | —C$_2$H$_5$ | 1 |  | | | 1 | 225–7 | 47.67<br>47.62 | 4.92<br>4.84 | 11.12<br>11.18 | 3,375<br>3,200<br>1,742 |

-continued

COMPOUND $$HN \diagdown \atop H_2N / C-N-CH_2CH_2CH_2CHCON \atop H \qquad R_1 \qquad R_2 \\ H-N-SO_2 \quad (CH_2)_n-COOR_3 \quad (I) \\ \qquad R_1$$

| Sample No. | $R_1$ | $R_2$ | $R_3$ | n | Addition moeity | Concentration Required to Prolong The Coagulation Time By A Factor of Two ($\mu$M) | Preparation Process (Ex. No.) | m.p. (°C) | Elemental Analysis Upper: Calculated Lower: Found | | | I.R. (KBr) (cm$^{-1}$) |
|---|---|---|---|---|---|---|---|---|---|---|---|---|
| | | | | | | | | | C | H | N | |
| 25 | naphthyl-OCH$_3$, OCH$_3$ | —(CH$_2$)$_3$—CH$_3$ | H | 1 | — | 2 | 3 | powder | 53.62 53.58 | 6.56 6.48 | 13.03 12.94 | 3,380 3,200 1,630 |
| 26 | " | —(CH$_2$)$_3$—CH$_3$ | —C(CH$_3$)$_3$ | 1 | ½H$_2$SO$_4$ | | 3 | 224 | 52.98 52.73 | 7.00 7.00 | 11.04 10.82 | 3,360 3,160 1,740 1,370 |
| 27 | naphthyl-OC$_2$H$_5$, OC$_2$H$_5$ | —CH$_2$CH$_2$OCH$_3$ | H | 1 | — | 15 | 3 | powder | 52.89 52.77 | 6.57 6.80 | 12.34 12.59 | 3,380 3,200 1,625 |
| 28 | " | —CH$_2$CH$_2$OCH$_3$ | —C(CH$_3$)$_3$ | 1 | ½H$_2$SO$_4$ | | 3 | powder | 52.39 | 6.97 | 10.54 | 3,370 3,150 1,740 |
| 29 | " | —(CH$_2$)$_3$CH$_3$ | H | 1 | — | | 3 | powder | 52.10 55.20 | 6.84 6.95 | 10.21 12.38 | 3,360 3,150 |
| 30 | " | —(CH$_2$)$_3$CH$_3$ | —C(CH$_3$)$_3$ | 1 | ½H$_2$SO$_4$ | | 3 | powder | 55.00 54.36 | 6.81 7.30 | 12.21 10.57 | 3,370 3,200 1,620 |
| 31 | naphthyl-OCH$_3$ | —(CH$_2$)$_3$CH$_3$ | H | 1 | — | 0.5 | 3 | powder | 54.25 | 7.11 | 10.81 | 3,200 1,735 |
| 32 | " | —(CH$_2$)$_3$CH$_3$ | —C(CH$_3$)$_3$ | 1 | ½H$_2$SO$_4$ | | 3 | powder | 54.43 54.21 | 6.55 6.50 | 13.80 13.79 | 3,360 3,180 1,632 |
| 33 | " | —CH$_2$CH$_2$OCH$_3$ | H | 1 | — | | 3 | powder | 53.63 53.50 | 7.00 6.79 | 11.58 11.40 | 3,380 3,200 1,370 |
| 34 | " | —CH$_2$CH$_2$OCH$_3$ | —C(CH$_3$)$_3$ | 1 | ½H$_2$SO$_4$ | | 3 | powder | 51.86 51.64 55.21 | 6.13 6.09 6.95 | 13.75 13.84 12.38 | 3,370 3,200 1,625 3,380 |
| 35 | naphthyl-OCH$_3$ | —CH$_2$CH$_2$OCH$_3$ | H | 1 | — | 0.5 | 2 | powder | 55.11 51.86 | 6.76 6.13 | 12.27 13.75 | 3,180 1,738 3,368 3,370 3,160 |
| 36 | " | —CH$_2$CH$_2$OCH$_3$ | —C$_2$H$_5$ | 1 | naphthyl with OH, NO$_2$, NO$_2$, HO$_3$S | | 2 | 158–150 | 51.72 47.94 47.83 | 6.11 4.85 4.80 | 13.63 11.51 11.43 | 1,620 3,375 3,200 1,740 |

-continued

Compound structure:

$$\underset{H_2N}{\overset{HN}{\diagdown}}C-N-CH_2CH_2CH_2CHCON\underset{R_1}{\overset{R_2}{\diagdown}}(CH_2)_n-COOR_3 \quad (I)$$
with H—N—SO₂ on the side chain.

| Sample No. | R₁ | R₂ | R₃ | n | Addition moiety | Concentration Required to Prolong The Coagulation Time By A Factor of Two (μM) | Preparation Process (Ex. No.) | m.p. (°C) | Elemental Analysis Upper: Calculated Lower: Found C | H | N | I.R. (KBr) (cm⁻¹) |
|---|---|---|---|---|---|---|---|---|---|---|---|---|
| 37 | " | —(CH₂)₂CH₃ | H | 1 | — | | 3 | powder | 53.53 | 6.33 | 14.19 | 3,375; 3,150 |
| 38 | " | —(CH₂)₂CH₃ | —C(CH₃)₃ | 1 | ½H₂SO₃ | | 3 | powder | 53.40 / 52.86 | 6.21 / 6.83 | 14.04 / 11.86 | 1,620; 3,380; 3,200; 1,740 |
| 39 | " | —(CH₂)₃CH₃ | H | 1 | — | 0.5 | 3 | powder | 52.77 / 54.43 | 6.66 / 6.55 | 11.75 / 13.80 | 1,370; 3,380; 3,150 |
| 40 | " | —(CH₂)₃CH₃ | —C(CH₃)₃ | 1 | ½H₂SO₃ | | 3 | 131–137 (dec.) | 54.22 / 53.63 | 6.31 / 7.00 | 13.59 / 11.58 | 1,620; 3,380; 3,160 |
| 41 | " | —(CH₂)₄CH₃ | H | 1 | — | | 3 | powder | 53.40 | 7.10 | 11.40 | 1,750; 1,640 |
| 42 | " | —(CH₂)₄CH₃ | —C(CH₃)₃ | 1 | ½H₂SO₃ | | 3 | 169–175 (dec.) | 55.26 | 6.76 | 13.43 | 3,350; 1,630 |
| | | | | | | | | | 55.21 / 54.35 | 6.65 / 7.17 | 13.29 / 11.32 | 3,350; 3,180 |
| 43 | " | —CH₂CH₂OCH₃ | H | 1 | — | 2.5 | 3 | powder | 54.27 | 7.00 | 11.08 | 1,740; 1,640 |
| 44 | " | —CH₂CH₂OCH₃ | —C(CH₃)₃ | 1 | ½H₂SO₃ | | 3 | powder | 51.86 / 51.77 | 6.13 / 6.00 | 13.75 / 13.72 | 3,365; 3,200; 1,620 |
| 45 | " | —(CH₂)₃CH₃ | H | 1 | — | | 3 | powder | 51.47 / 51.20 | 6.65 / 6.35 | 11.54 / 11.24 | 3,370; 3,200; 1,370 |
| 46 | " | —(CH₂)₃CH₃ | —C(CH₃)₃ | 1 | ½H₂SO₃ | | 3 | powder | 54.43 | 6.55 | 13.80 | 3,375; 3,200 |
| | | | | | | | | | 54.28 / 53.63 | 6.31 / 7.00 | 13.70 / 11.58 | 1,622; 3,380; 3,200 |
| 47 | " | —CH₂CH₂OCH₃ | H | 2 | — | | 3 | powder | 53.53 | 7.08 | 11.40 | 1,740; 1,370 |
| 48 | " | —CH₂CH₂OCH₃ | —C(CH₃)₃ | 2 | ½H₂SO₃ | | 3 | powder | 52.76 | 6.35 | 13.38 | 3,375; 3,180 |
| | | | | | | | | | 52.47 / 52.24 | 6.01 / 6.82 | 13.09 / 11.28 | 1,620; 3,380; 3,200; 1,740 |
| 49 | (1-naphthyl with OCH₃) | —CH₂CH₂CO₂C₂H₅ | H | 1 | — | 6.5 | 3 | powder | 52.00 / 54.63 | 6.55 / 6.42 | 11.00 / 12.74 | 1,368; 3,350 (broad) |
| 50 | " | —CH₂CH₂OCH₃ | —n-C₈H₁₇ | 1 | HCl | 2 | 5 | powder | 54.28 | 6.31 | 12.53 | 1,740 |
| | | | | | | | | | 54.10 | 7.32 | 10.18 | 3,180 |

-continued

COMPOUND $$HN=\overset{H}{\underset{H_2N}{C-N-CH_2CH_2CH_2CHCON}}\overset{R_2}{\underset{R_1}{(CH_2)_n-COOR_3}} \quad (I)$$

$$H-N-SO_2$$

| Sample No. | R₁ | R₂ | R₃ | n | Addition moeity | Concentration Required to Prolong The Coagulation Time By A Factor of Two (μM) | Preparation Process (Ex. No.) | m.p. (° C) | Elemental Analysis Upper: Calculated Lower: Found | | | I.R. (KBr) (cm⁻¹) |
|---|---|---|---|---|---|---|---|---|---|---|---|---|
| | | | | | | | | | C | H | N | |
| 51 | 2,3-(OCH₃)₂-naphthyl | —CH₂CH₂OCH₃ | —CH₂—C₆H₅ | 1 | — | | 4 | powder | 53.81 57.22 | 7.13 6.24 | 9.93 11.12 | (broad) 1,740 1,630 3,300 3,150 |
| 52 | " | —CH₂CH₂OCH₃ | —CH₂—C₆H₄—CH₃ | 1 | HCl | 20 | 5 | powder | 56.98 54.09 | 6.18 6.05 | 11.31 10.51 | 1,740 1,650 3,250 3,100 |
| 53 | " | —CH₂CH₂OCH₃ | indanyl | 1 | HCl | 30 | 5 | powder | 53.83 55.53 | 5.97 6.12 | 10.36 10.12 | 1,740 1,640 3,350 3,150 |
| 54 | " | —CHCH₂CH₂COOH / OCH₃ | —NH₄ | 1 | — | 55 | 4 | powder | 55.37 50.15 49.91 | 6.01 6.41 6.35 | 10.01 14.04 13.83 | 1,740 1,650 3,280 1,620 |
| 55 | " | —CH₂CHCH₃ / OH | H | 1 | — | 6.5 | 4 | powder | 52.06 52.40 | 6.38 6.37 | 12.65 12.73 | 3,350 (broad) 1,620 |
| 56 | " | —CH₂CH₂CHCH₃ | H | 1 | — | | 3 | powder | 52.07 | 6.37 | 12.65 | 3,350 (broad) 1,620 |
| 57 | " | —CH₂CH₂SOCH₃ | H | 1 | — | 6.5 | 3 | powder | 51.95 48.78 | 6.27 5.77 | 12.84 12.93 | 3,320 1,620 1,390 |
| 58 | " | —CH₂CH₂OH | H | 1 | — | | 3 | powder | 45.54 50.27 | 5.76 5.95 | 13.15 13.33 | 3,390 1,630 1,260 1,160 |
| 59 60 61 | " " " | —CH₃CH=CH₂ =CH₂C≡CH —COOH —CH—CH₂—C₆H₅ | H H —NH₄ | 1 1 | | | 3 3 4 | powder | 50.11 52.95 53.16 53.85 53.61 | 5.87 6.00 5.64 5.93 5.76 | 13.34 13.43 13.48 13.00 12.84 | 3,320 1,610 |

EXAMPLE 6

Tablets Suitable for Oral Administration

Tablets containing the ingredients indicated below may be prepared by conventional techniques.

| Ingredient | Amount per tablet (mg) |
|---|---|
| $N^2$-(7-methoxy-2-naphthylsulfonyl)-L-arginyl-N-(2-methoxyethyl)glycine | 250 |
| Lactose | 140 |
| Corn Starch | 35 |
| Talcum | 20 |
| Magnesium stearate | 5 |
| Total | 450 mg |

EXAMPLE 7

Capsules for Oral Administration

Capsules of the below were made up by thoroughly mixing together batches of the ingredients and filling hard gelatin capsules with the mixture.

| Ingredient | Amount per capsule (mg) |
|---|---|
| $N^2$-(7-methoxy-2-naphthylsulfonyl)-L-arginyl-N-(2-methoxyethyl)glycine | 250 |
| Lactose | 250 |
| Total | 500 mg |

EXAMPLE 8

Sterile Solution for Infusion

The following ingredients are dissolved in water for intravenous perfusion and the resulting solution is then sterilized.

| Ingredients | Amount (g) |
|---|---|
| $N^2$-(7-methoxy-2-naphthylsulfonyl)-L-arginyl-N-(2-methoxyethyl)glycine | 25 |
| Buffer system | As desired |
| Glucose | 25 |
| Distilled water | 500 |

PREPARATION A

Alkoxynaphthalene Sulfonyl Chlorides (A) Sodium 6, 7-dimethoxy-2-naphthalenesulfonate To a well stirred solution of 70.8 g of sodium 6, 7-dihydroxy-2-naphthalenesulfonate and 77.2 g of sodium hydroxide in 450 ml of water was added dropwise 230 ml of dimethyl sulfate at 60° C over a period of 1 hour, during which time the product precipitated. To this reaction mixture was added in portions 38.8 g of sodium hydroxide, and stirring was continued for one hour. After one hour at room temperature, the precipitate was filtered, washed with ethanol an dried to give 50 g of sodium 6, 7-dimethoxy-2-naphthalenesulfonate.

(B) 6, 7-dimethoxy-2-naphthalenesulfonyl chloride

To a stirred suspension of 50 g of finely divided sodium 6, 7-dimethoxy-2-naphthalenesulfonate in 100 ml of dimethylformamide was added dropwise 62.2 ml of thionyl chloride at room temperature. After 30 minutes, the reaction mixture was poured into 1 l of ice water, and the precipitate filtered and then dissolved into 250 ml of benzene. The benzene solution was repeatedly washed with water and dried over anhydrous sodium sulfate. The solvent was evaporated to dryness in vacuo, and the residue was recrystallized from benzene-n-hexane (1:1) to give 32 g of 6, 7-diemthoxy-2-naphthalenesulfonyl chloride, M.P. 127.5°–129.5° C.

Analysis—Calcd. for $C_{12}H_{11}O_4SCl$ (percent): C, 50.26; H, 3.87; Cl, 12.37 Found (percent) : C, 50.45; H, 4.00; Cl, 12.33. The following alkoxynaphthalene sulfonyl chlorides not previously reported in the chemical literature were synthesized by the aforementioned procedure which is essentially that as described in E. H. Rodd, "Chemistry of Carbon Compounds", Elsevier Publishing Company, 1954, Vol. III, P. 441–469.

| No. | Arylsulfonyl Chloride | M.P. (° C) |
|---|---|---|
| 1 | ClO$_2$S-naphthalene-OC$_2$H$_5$, OC$_2$H$_5$ | 118 – 119.5 |
| 2 | ClO$_2$S-naphthalene-OCH$_3$, OCH$_3$ | 136.5 – 138.5 |
| 3 | ClO$_2$S-naphthalene-O-O (dioxole) | 137 – 139 |

PREPARATION B

Amino Acid Derivatives (A) N-butylglycine tert-butyl ester

To 36.5 g of butylamine was added with stirring 15.05 g of tert-butyl chloroacetate over a period of 30 minutes, while maintaining the temperature at 30°–70° C. The reaction mixture was held at 70° C for an additional 1 hour. At the end of this period, the excess butyl amine was evaporated in vacuo, and the residue was taken up in 40 ml of 2N NaOH solution and 50 ml of benzene, transferred into a separatory funnel and well shaken. The benzene solution was separated, washed with water, dried over anhydrous sodium sulfate and filtered. After evaporation of benzene, the residue was distilled under reduced pressure to give 17.0 g (90.0 percent) of N-butylglycine tert-butyl ester, B.P. 76° C/4 mmHg.

The following amino acid tert-butyl esters not previously reported in the chemical literature were synthesized by the aforementioned procedure which is essentially that as taught by A. J. Speziale et al., J. Org. Chem. 25 731 (1960).

| No. | Amino Acid Derivative | B.P. |
|---|---|---|
| 1 | HN(-(CH$_2$)$_2$CH$_3$)(CH$_2$CO$_2$-t-C$_4$H$_9$) | 95° C/20 mmHg |
| 2 | HN(-CH$_2$CH(CH$_3$)$_2$)(CH$_2$CO$_2$-t-C$_4$H$_9$) | 65° C/5 mmHg |
| 3 | HN(-(CH$_2$)$_4$CH$_3$)(CH$_2$CO$_2$-t-C$_4$H$_9$) | 89 – 90° C/2.5 mmHg |
| 4 | HN(-(CH$_2$)$_5$CH$_3$)(CH$_2$CO$_2$-t-C$_4$H$_9$) | 83 – 5° C/1.5 mmHg |

-continued

| No. | Amino Acid Derivative | B.P. |
|---|---|---|
| 5 | HN<(CH$_2$)$_7$CH$_3$ / CH$_2$CO$_2$-t-C$_4$H$_9$ | 125 - 130° C/4 mmHg |
| 6 | HN<CH$_2$CH$_2$OCH$_3$ / CH$_2$CO$_2$-t-C$_4$H$_9$ | 61 - 2° C/2 mmHg |
| 7 | HN<CH$_2$CH$_2$OCH$_3$ / CH$_2$CH$_2$CO$_2$-t-C$_4$H$_9$ | 94° C/3 mmHg |
| 8 | HN<CH$_2$CH$_2$OCH$_3$ / CH$_2$CH$_2$CH$_2$CO$_2$-t-C$_4$H$_9$ | 60 - 3° C/3 mmHg |
| 9 | HN<CH$_2$CH$_2$CH$_2$OCH$_3$ / CH$_2$CO$_2$-t-C$_4$H$_9$ | 95 - 7° C/5 mmHg |
| 10 | HN<CH$_2$CH$_2$OCH$_2$CH$_3$ / CH$_2$CH$_2$CO$_2$-t-C$_4$H$_9$ | 102° C/4 mmHg |
| 11 | HN<CH$_2$CH$_2$CO$_2$C$_2$H$_5$ / CH$_2$CO$_2$-t-C$_4$H$_9$ | 115° C/2 mmHg |
| 12 | HN<CH$_2$CH$_2$CHCH$_3$(OH) / CH$_2$CO$_2$-t-C$_4$H$_9$ | 82 - 84° C/2 mmHg |
| 13 | HN<CH$_2$CH$_2$SOCH$_3$ / CH$_2$CO$_2$-t-C$_4$H$_9$ | 150° C/0.5 mmHg |
| 14 | HN<CH$_2$CH$_2$OH / CH$_2$CO$_2$-t-C$_4$H$_9$ | 95 - 6° C/2 mmHg |
| 15 | HN<CH$_2$C≡CH / CH$_2$CO$_2$-t-C$_4$H$_9$ | |

(B) N-(2-methoxyethyl)glycine ethyl ester

To a stirred solution of 165.2 g of 2-methoxyethylamine and 202.4 g of triethylamine in 1 l of benzene was added dropwise to a solution of 334.0 g of ethyl bromoacetate in 200 ml of benzene in 1 hour at room temperature. At the end of this period, the mixture was heated at reflux for 2 hours to complete the reaction. Upon chilling, the triethylamine hydrochloride was removed by filtration and washed with benzene. After removal of the solvent, the product was distilled in vacuo to yield 242.8 g (75.3 percent) of N-(2-methoxyethyl)glycine ethyl ester, B. P. 73°-5° C/4 mmHg.

The following amino acid ethyl esters not previously reported in the chemical literature were synthesized by the aforementioned procedure which is essentially that as taught by A. J. Speziale et al., J. Org. Chem., 25 731 (1960).

| No. | Amino Acid Ethyl Ester | M.P. (° C) or B.P. (° C/mmHg) |
|---|---|---|
| 1 | HN<CH$_2$CH$_2$OCH$_3$ / CH$_2$CH$_2$CO$_2$C$_2$H$_5$ | 63 - 4° C/3 mmHg |
| 2 | HN<CH(CO$_2$C$_2$H$_5$)CH$_2$CH$_2$CH$_3$ / CH$_2$CO$_2$C$_2$H$_5$ | 113 - 6° C/3 mmHg |
| 3 | HN<CH(CO$_2$C$_2$H$_5$)CH$_2$—C$_6$H$_5$ / CH$_2$CO$_2$C$_2$H$_5$ | 116 - 7° C/1 mmHg |
| 4 | HN<CH$_2$CHCH$_3$(OCH$_3$) / CH$_2$CO$_2$C$_2$H$_5$ | 78 - 80° C/2 mmHg |

Having now fully described the invention, it will be apparent to one of ordinary skill in the art that many changes and modification can be made thereto without departing from the spirit or scope of the invention as set forth herein.

What is claimed as new and desired to be secured by Letters Patent of the United States is:

1. N$^2$-alkoxynaphthylsulfonyl-L-argininamides having the formula:

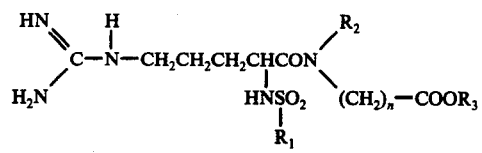

and the pharmaceutically acceptable salts thereof, wherein R$_1$ is naphthyl substituted with at least one C$_1$-C$_5$ alkoxy; R$_2$ is selected from the group consisting of C$_2$-C$_{10}$ alkyl, C$_3$-C$_{10}$ alkenyl, C$_3$-C$_{10}$ alkynyl, C$_2$-C$_{10}$ alkoxyalkyl, C$_8$-C$_{15}$ α-carboxyaralkyl, C$_2$-C$_{10}$ alkylsulfinylalkyl, C$_1$-C$_{10}$ hydroxyalkyl, C$_2$-C$_{10}$ carboxyalkyl, C$_3$-C$_{10}$ alkoxycarbonylalkyl and C$_1$-C$_{10}$ haloalkyl; R$_3$ is selected from the group consisting of hydrogen, C$_1$-C$_{10}$ alkyl, C$_6$-C$_{10}$ aryl, C$_7$-C$_{12}$ aralkyl and 5-indanyl; and n is an integer of 1, 2 or 3.

2. The compound of claim 1, wherein R$_1$ is naphthyl substituted with at least one C$_1$-C$_5$ alkoxy; R$_2$ is selected from the group consisting of C$_2$-C$_{10}$ alkyl, C$_3$-C$_6$ alkenyl, C$_3$-C$_6$ alkynyl, C$_2$-C$_6$ alkoxyalkyl, C$_8$-C$_{12}$ αcarboxyaralkyl, C$_2$-C$_6$ alkylsulfinylalkyl, C$_1$-C$_6$ hydroxyalkyl, C$_2$-C$_7$ carboxyalkyl, C$_3$-C$_8$ alkoxycarbonylalkyl and C$_1$-C$_5$ haloalkyl; R$_3$ is selected from the group consisting of hydrogen, C$_1$-C$_{10}$ alkyl, C$_6$-C$_{10}$ aryl, C$_{7-10}$ aralkyl and 5-indanyl; and n is an integer of 1, 2 or 3.

3. The compound of claim 2, wherein R$_2$ is selected from the group consisting of 5-methoxy-1-naphthyl, 6-methoxy-2-naphthyl, 7-methoxy-2-naphthyl, 4, 6-dimethoxy-2-naphthyl, 6,7-dimethoxy-2-naphthyl and 6, 7-diethoxy-2-naphthyl; R$_2$ is selected from the group consisting of propyl, butyl, isobutyl, pentyl, hexyl, octyl, 2-methoxyethyl, 2-ethoxyethyl, 3-methoxypropyl, 2-methoxypropyl, allyl, 2-propynyl, α-carboxyphenethyl, 2-methysulfinylethyl, 2-hydroxyethyl, 3-hydroxybutyl, 1-carboxybutyl and 2-ethoxycarbonylethyl; and R$_3$ is selected from the group consisting of hydrogen, ethyl, tert-butyl, octyl, phenyl, m-tolyl, benzyl and 5-indanyl.

4. The compound of claim 1, which is N$^2$-(6, 7-dimethoxy-2-naphthylsulfonyl)-L-arginyl-N-butylglycine.

5. The compound of claim 1, which is N$^2$-(7-methoxy-2-naphthylsulfonyl) L-arginyl-N-butylglycine.

6. The compound of claim 1, which is N$^2$-(6, 7-dimethoxy-2-naphthylsulfonyl)-L-arginyl-N-(2-methoxyethyl)glycine.

7. The compound of claim 1, which is N$^2$-(6, 7-dimethoxy-2-naphthylsulfonyl)-L-arginyl-N-(2-methoxyethyl)glycine ethyl ester.

8. The compound of claim 1, which is N²-(4,6-dimethoxy-2-naphthylsulfonyl)-L-arginyl-N-(2-methoxyethyl)glycine.

9. The compound of claim 1, which is N²-(7-methoxy-2-naphthylsulfonyl)-L-arginyl-N-(2-methoxyethyl)glycine.

10. A method for inhibiting activity and suppressing activation of thrombin in vivo in mammals which comprises administering to a mammal a pharmaceutically effective amount of an N²-alkoxynaphthylsulfonyl-L-argininamide having the formula:

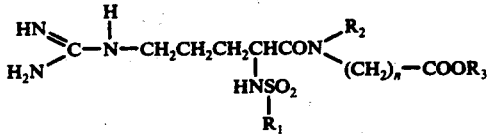

or the pharmaceutically acceptable salts thereof wherein $R_1$ is naphthyl substituted with at least one $C_1$–$C_5$ alkoxy; $R_2$ is selected from the group consisting of $C_2$–$C_{10}$ alkyl, $C_3$–$C_{10}$ alkenyl, $C_3$–$C_{10}$ alkynyl, $C_2$–$C_{10}$ alkoxyalkyl, $C_{8-15}$ α-carboxyaralkyl, $C_2$–$C_{10}$ alkylsulfinylalkyl, $C_1$–$C_{10}$ hydroxyalkyl, $C_2$–$C_{10}$ carboxyalkyl, $C_3$–$C_{10}$ alkoxycarbonylalkyl and $C_1$–$C_{10}$ haloalkyl; $R_3$ is selected from the group consisting of hydrogen, $C_1$–$C_{10}$ alkyl, $C_6$–$C_{10}$ aryl, $C_7$–$C_{12}$ aralkyl and 5-indanyl; and $n$ is an integer of 1, 2 or 3.

* * * * *

UNITED STATES PATENT AND TRADEMARK OFFICE
CERTIFICATE OF CORRECTION

PATENT NO. : 4,073,892
DATED : February 14, 1978
INVENTOR(S) : Okamoto et al

It is certified that error appears in the above-identified patent and that said Letters Patent are hereby corrected as shown below:

Under the Foreign Application Priority Data, the last three dates and corresponding application numbers have been omitted.

Accordingly, please inser the following:

--Mar. 5, 1975   Japan...........50-026768
　Mar. 11, 1975  Japan...........50-029357
　Mar. 11, 1975  Japan...........50-029358--

*Signed and Sealed this*

*Eleventh* Day of *July 1978*

[SEAL]

Attest:

RUTH C. MASON
*Attesting Officer*

DONALD W. BANNER
*Commissioner of Patents and Trademarks*